United States Patent

Yamada et al.

[11] Patent Number: 5,863,785
[45] Date of Patent: Jan. 26, 1999

[54] DECARBAMYLASE ISOLATED FROM COMAMONAS OR BLASTOBACTER

[75] Inventors: Hideaki Yamada; Sakayu Shimizu, both of Kyoto; Yasuhiro Ikenaka; Kazuyoshi Yajima, both of Akashi; Yukio Yamada, Kakogawa; Hirokazu Nanba, Takasago; Masayuki Takano, Akashi; Satomi Takahashi, Kobe, all of Japan

[73] Assignee: Kanegafuchi Chemical Industry Co., Ltd., Osaka, Japan

[21] Appl. No.: 479,639

[22] Filed: Jun. 7, 1995

Related U.S. Application Data

[62] Division of Ser. No. 244,657, Jun. 6, 1994.

[30] Foreign Application Priority Data

Oct. 5, 1992 [JP] Japan .................................. 4-265914

[51] Int. Cl.$^6$ .............................. C12N 9/78; C12N 9/80
[52] U.S. Cl. ........................................... 435/227; 435/228
[58] Field of Search ...................................... 435/227, 228

[56] References Cited

U.S. PATENT DOCUMENTS

| | | | |
|---|---|---|---|
| 4,211,840 | 7/1980 | Nakamori et al. | 435/107 |
| 4,242,452 | 12/1980 | Yamada et al. | 435/117 |
| 4,312,948 | 1/1982 | Olivieri et al. | 435/253 |
| 5,565,344 | 10/1996 | Nanba et al. | 435/106 |

FOREIGN PATENT DOCUMENTS

| | | |
|---|---|---|
| 0 046 186 | 2/1982 | European Pat. Off. . |
| 55-88697 | 7/1980 | Japan . |
| 57-18793 | 4/1982 | Japan . |
| 61-09292 | 1/1986 | Japan . |
| 62-25990 | 2/1987 | Japan . |
| 1-71477 | 3/1989 | Japan . |
| 1-48758 | 10/1989 | Japan . |

OTHER PUBLICATIONS

Ogawa et al., J. Biotechnol. 38: 11–19 (1994).
Ogawa et al., Eur. J. Biochem. 212: 685–691 (1993).
ATCC Catalogue of Bacteria and Bacteriophages (1992).
Yokozeki et al., Agric. Biol. Chem. 51: 721–728 (1987).
Nichols et al., Plant Growth Regul. 12(3): 237–244 (1993).

*Primary Examiner*—Sandra E. Saucier
*Attorney, Agent, or Firm*—Foley & Lardner

[57] ABSTRACT

In a process for the production of a D-α-amino acid, in which an N-carbamyl-D-α-amino acid corresponding to the general formula:

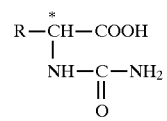

wherein R represents phenyl, hydroxy-substituted phenyl, substituted or unsubstituted alkyl, or thienyl, is converted by a microbial enzyme in an aqueous medium to a D-α-amino acid corresponding to the general formula:

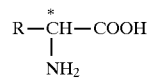

wherein R is the same as defined above, decarbamylase produced by a microorganism of the genus Comamonas, Blastobacter, Alcaligenes, Sporosarcina, Rhizobium, Bradyrhizobium or Arthrobacter is used as the enzyme converting the N-carbamyl-D-α-amino acid to the D-α-amino acid.

The conversion of the N-carbamyl-D-α-amino acids to the D-α-amino acids is carried out in a neutral to alkaline pH range.

4 Claims, 12 Drawing Sheets a: COMAMONS SP. E 222 DECARBAMYLASE, PURIFIED
b: MW MARKERS

● : Comamonas sp. E 222 c decarbamylase
○ : MW Markers
    Aldolase:                158,000 Da
    Bovine serum albumin:  68,000 Da
    Ovalbumin:           45,000 Da
    Chymotrypsinogen A:   25,000 Da
    Cytochrome C:        12,500 Da a: MW MARKER
b: BLASTOBACTER SP. A 17 P-4 DECARBAMYLASE, PURIFIED ● : Blastobacter sp. A 17 p-4 decarbamylase
○ : MW Markers
    Aldolase:                     158,000 Da
    Bovine serum albumin:   68,000 Da
    Ovalbumin:               45,000 Da
    Chymotrypsinogen A:    25,000 Da
    Cytochrome C:         12,500 Da

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 30 amino acids
( B ) TYPE: amino acid
( D ) TOPOLOGY: linear ( x i ) SEQUENCE DESCRIPTION: SEQ ID NO:1:

Ser Arg Ile Val Asn Tyr Ala Ala Ala Gln Leu Gly Pro Ile Gln Arg
1               5                   10                  15

Ala Asp Ser Arg Ala Asp Val Met Glu Arg Leu Leu Ala His
            20              25                  30

( 2 ) INFORMATION FOR SEQ ID NO:2:

( i ) SEQUENCE CHARACTERISTICS:
( A ) LENGTH: 40 amino acids
( B ) TYPE: amino acid
( D ) TOPOLOGY: linear ( x i ) SEQUENCE DESCRIPTION: SEQ ID NO:2:

Ala Arg Lys Leu Asn Leu Ala Val Ala Gln Leu Gly Pro Ile Ala Arg
1               5                   10                  15

Ala Glu Thr Arg Asp Gln Val Val Ala Arg Leu Met Glu Met Met Lys
            20              25                  30

Glu Ala Lys Ser Ser Arg Gly Thr
            35              40

( 2 ) INFORMATION FOR SEQ ID NO:3:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:3:

Thr Arg Gln Met Ile Leu Ala Val Gly Gln
1               5                   10

DECARBAMYLASE ISOLATED FROM COMAMONAS OR BLASTOBACTER

This application is a divisional of application Ser. No. 08/244,657, filed Jun. 6, 1994.

FIELD OF THE INVENTION

The present invention relates to a process for the production of a D-α-amino acid, in which a D-N-carbamyl-α-amino acid corresponding to the general formula:

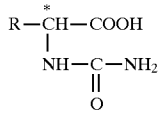

wherein R represents phenyl, hydroxy-substituted phenyl, substituted or unsubstituted alkyl preferably having 1 to 5 carbon atoms, or thienyl, is converted by an enzyme having an ability to eliminate the carbamyl group (hereinafter referred to as "decarbamylase") to a D-α-amino acid corresponding to the formula:

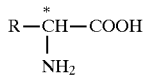

wherein R is the same as defined above.

These optically active D-α-amino acids are important as pharmaceutical intermediates. In particular, D-phenylglycine and D-(4-hydroxyphenyl)glycine (hereinafter referred to as "D-HPG") are useful for the production of semi-synthetic penicillin and semi-synthetic cephalosporin.

PRIOR ART

Production of D-α-amino acids by eliminating carbamyl groups from corresponding D-N-carbamyl-α-amino acids has been known. The elimination has been done chemically (Japanese Patent Publication No. 4707/1983) or by enzymatic reactions of microorganisms (Japanese Patent Publication Nos. 18793/1982, 20520/1988 and 48758/1989).

Most of these microbial enzymes have optimum pH values around a neutral range. However, in the previous step, wherein the N-carbamyl-D-α-amino acids are prepared by selectively hydrolyzing the D-form of corresponding DL-5-substituted hydantoins, hydantoin hydrolase having optimum pH of from 8 to 9 is used. Therefore, the subsequent conversion of the N-carbamyl-D-α-amino acids to D-α-amino acids by decarbamylase has to be carried out in a different reaction medium from that in the previous step.

SUMMARY OF THE INVENTION

The present inventors made a search for microorganisms which could enzymatically eliminate carbamyl groups ("decarbamylation") from D-N-carbamyl-α-amino acids to form D-α-amino acids, mainly among the genera which are unknown to have decarbamylase. It has now been found that the bacteria of the genera Comamonas, Blastobacter, Alcaligenes, Sporosarcina, Rhizobium, Bradyrhizobium and Arthrobacter have the decarbamylase activity.

Accordingly, the present invention relates to a process for the production of a D-α-amino acid, in which an N-carbamyl-D-α-amino acid corresponding to the general formula (I):

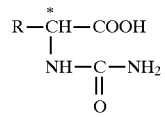

wherein R represents phenyl, hydroxy-substituted phenyl, substituted or unsubstituted alkyl preferably having 1 to 5 carbon atoms, or thienyl, is converted by a microbial enzyme in an aqueous medium to a D-α-amino acid corresponding to the general formula (II):

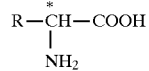

wherein R is the same as defined above, characterized in that the enzyme is decarbamylase produced by a microorganism of the genus Comamonas, Blastobacter, Alcaligenes, Sporosarcina, Rhizobium, Bradyrhizobium or Arthrobacter.

DETAILED EXPLANATION OF THE INVENTION

Figure 1:
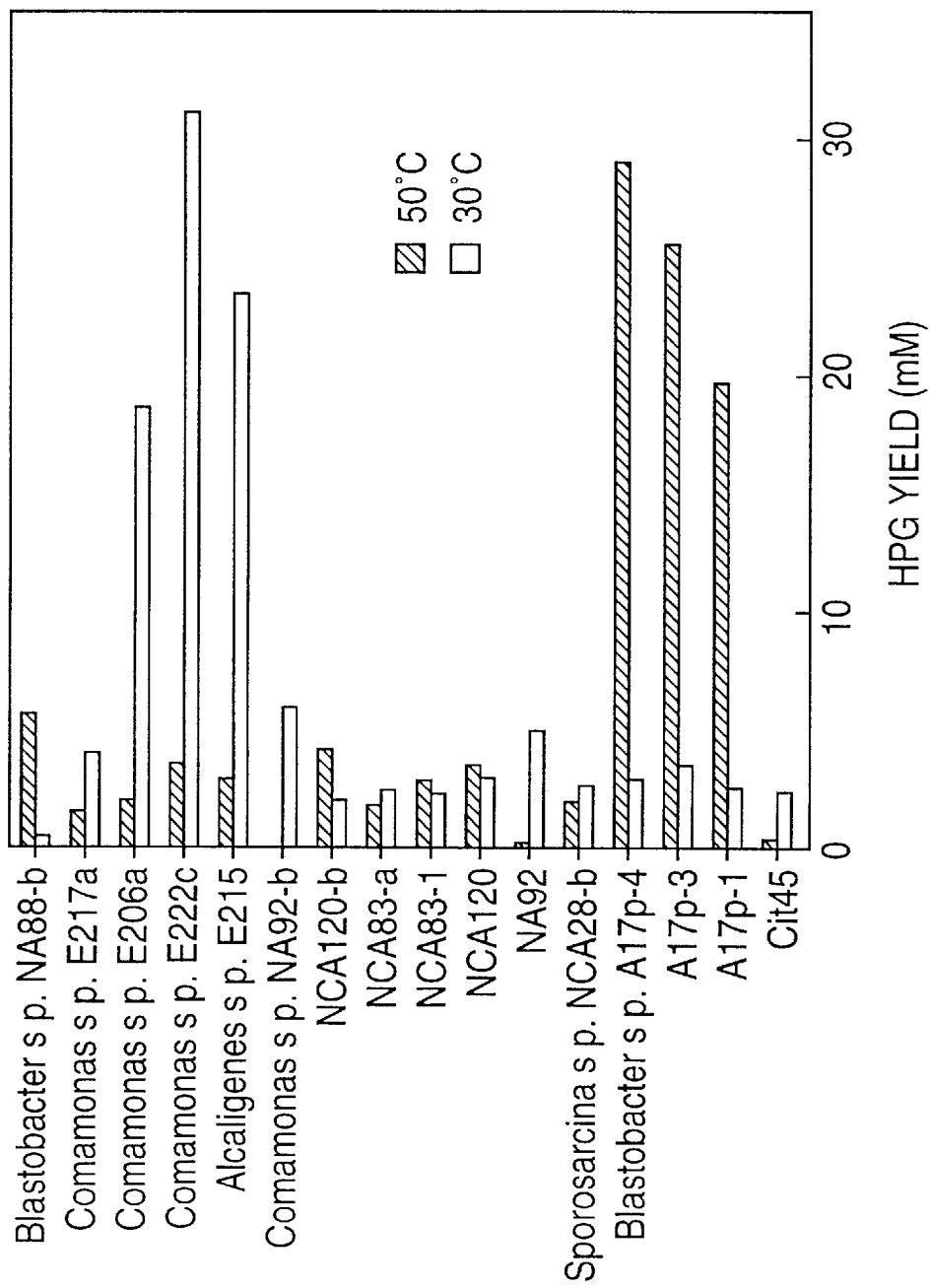
FIG. 1 is a graph showing the results of decarbamylation at 50° C. and 30° C. by newly screened strains.

According to the present invention, both D-isomer specific decarbamylase and unspecific decarbamylase may be actually used. An enzyme which is strictly stereoselective to D-N-carbamyl-α-amino acids is often called D-N-carbamyl-α-amino acid amide hydrolase.

Among the microorganisms according to the present invention, strains showing particularly high decarbamylase activity are, for example, Comamonas sp. E 222 C (FERM BP No. 4411, National Institute of Bioscience and Human-Technology, Agency of Industrial Science and Technology, 1–3, Higashi 1-chome, Tsukuba-shi, Ibaraki-ken, 305, Japan, Sep. 18, 1992), Comamonas sp. E 206 a, Comamonas sp. E 217 a, Blastobacter sp. NA 88-b, Blastobacter sp. A 17 p-4 (FERM BP No. 4410, National Institute of Bioscience and Human-Technology, Agency of Industrial Science and Technology, Sep. 18, 1992), Alcaligenes sp. E 215 (FERM BP No. 4409, National Institute of Bioscience and Human-Technology, Agency of Industrial Science and Technology, Sep. 18, 1992), *Alcaligenes xylosoxidans* subsp. *denitrificans* CL 66-2 a, Sporosarcina sp. NCA 28-b (FERM BP No. 4408, National Institute of Bioscience and Human-Technology, Agency of Industrial Science and Technology, Sep. 24, 1992), Rhizobium sp. KNK 1415 (FERM BP No. 4419, National Institute of Bioscience and Human-Technology, Agency of Industrial Science and Technology, Sep. 22, 1993), *Bradyrhizobium japonicum* IFO 14783, Bradyrhizobium sp. IFO 15003, Arthrobacter sp. CA 17-2 (FERM BP No. 4420, National Institute of Bioscience and Human-Technology, Agency of Industrial Science and Technology, Sep. 22, 1993).

Typical examples of the strains Comamonas sp. E 222 C, Blastobacter sp. A 17 p-4, Alcaligenes sp. E 215, Sporosarcina sp. NCA 28-b, Rhizobium sp. KNK 1415 and Arthrobacter sp. CA 17-2 are microbiologically characterized as follows:

Comamonas sp. E 222 C (a) Morphology

Bacillus (bent), Gram-variable

Spore: −

Colony: buff, semi-translucent, round, regular, entire, shiny, low convex, smooth; diameter 1 mm (48 hr)

Growth (48 hr) at: 37° C.+

| (a) Morphology | |
| --- | --- |
| Bacillus (bent), Gram-variable | |
| Spore: | − |
| Colony: | buff, semi-translucent, round, regular, entire, shiny, low convex, smooth; diameter 1 mm (48 hr) |
| Growth (48 hr) at: | 37° C. + |
| | 41° C. − |
| | 45° C. − |
| (b) Physiological activities | |
| Catalase | + |
| Oxidase | − |
| Glucose fermentation | − |
| NO$_3$ Reduction | − |
| Indole production | − |
| Acid production from glucose | − |
| Arginine dehydrolase | − |
| Urease | − |
| Aesculin hydrolysis | − |
| Gelatin hydrolysis | − |
| β-Galactosidase | − |
| Cytochrome oxidase | + (weak) |
| (c) Assimilation | |
| Glucose | − |
| Arabinose | − |
| Mannose | − |
| Mannitol | − |
| N-Acetylglucosamine | − |
| Maltose | − |
| Gluconic acid | + |
| Caproic acid | + |
| Adipic acid | − |
| Malic acid | + |
| Citric acid | + |
| Phenyl acetate | + |

Blastobacter sp. A 17 p-4

(a) Morphology

Bacillus (oval), Gram-negative

Spore: −

Colony: white, semi-translucent, round, regular, entire, shiny, low convex, smooth, mucoid producing; diameter 1.0–1.5 mm (48 hr)

| (a) Morphology | |
| --- | --- |
| Bacillus (oval), Gram-negative | |
| Spore: | − |
| Colony: | white, semi-translucent, round, regular, entire, shiny, low convex, smooth, mucoid producing; diameter 1.0–1.5 mm (48 hr) |
| Growth (48 hr) at: | 37° C. + |
| | 41° C. − |
| | 45° C. − |
| (b) Physiological activities | |
| Catalase | + |
| Oxidase | + (weak) |
| Glucose fermentation | − |
| NO$_3$ Reduction | − |
| Indole production | − |
| Acid production from glucose | − |
| Arginine dehydrolase | − |
| Urease | + |
| Aesculin hydrolysis | + |
| Gelatin hydrolysis | − |
| β-Galactosidase | + |
| Cytochrome oxidase | + |
| (c) Assimilation | |
| Glucose | + |
| Arabinose | + |
| Mannose | + |
| Mannitol | + |
| N-Acetylglucosamine | + |
| Maltose | + |
| Gluconic acid | − |
| Caproic acid | − |
| Adipic acid | − |
| Malic acid | − |
| Citric acid | − |
| Phenyl acetate | − |

Alcaligenes sp. E 215

(a) Morphology

Bacillus, Gram-variable

Spore: −

Mobility: +

Colony: buff, semi-translucent, round, regular, entire, low convex, shiny, smooth; diameter 1 mm (48 hr)

| (a) Morphology | |
| --- | --- |
| Bacillus, Gram-variable | |
| Spore: | − |
| Mobility: | + |
| Colony: | buff, semi-translucent, round, regular, entire, low convex, shiny, | smooth; diameter 1 mm (48 hr)
Growth (48 hr) at: 37° C. +
 41° C. −
 45° C. −

(b) Physiological activities

| | |
|---|---|
| Catalase | + |
| Oxidase | − |
| Glucose fermentation | − |

Sporosarcina sp. NCA 28-b (a) Morphology

Coccus, Gram-variable

Spore: +

Mobility: −

Colony: round, regular, entire, cream to white, semi-translucent; diameter <0.5 mm (48 hr)

| (a) Morphology | |
|---|---|
| Coccus, Gram-variable | |
| Spore: | + |
| Mobility: | − |
| Colony: | round, regular, entire, cream to white, semi-translucent; diameter <0.5 mm (48 hr) |
| Growth at: 37° C. − | |
|  45° C. − | |
| (b) Physiological activities | |
| Catalase | + |
| Oxidase | + |
| Glucose fermentation | − |

Rhizobium sp. KNK-1415 (FERM BP-4419)

| (a) Morphology | |
|---|---|
| Bacillus (short), Gram-negative | |
| Spore: | − |
| Flagellum: | polar or peritrichous |
| Colony: | off-white, opaque, entire, regular, smooth, low convex, mucoid producing; diameter 5 mm (5 days) |
| Growth at: | 30° C. + |
|  | 37° C. (±) |
| (b) Physiological activities | |
| Catalase | + |
| Oxidase | + |
| Glucose fermentation | − |
| NO₃ Reduction | + |
| Indole production | − |
| Acid production from glucose | − |
| Arginine dehydrolase | − |
| Urease | + |
| Aesculin hydrolysis | + |
| Gelatin hydrolysis | − |
| βGalactosidase | + |
| Cytochrome oxidase | + |
| 3-Ketolactose production | − |
| H₂S Production | − |
| (c) Assimilation | |
| Glucose | + |
| Arabinose | + |
| Mannose | + |
| Mannitol | + |
| N-Acetylglucosamine | + |
| Maltose | + |
| Gluconic acid | − |
| Caproic acid | − |
| Adipic acid | − |
| Malic acid | + |
| Citric acid | − |
| Phenyl acetate | − |

GC content: 63.4%

| Quinone analysis: | |
|---|---|
| Q-10 | 95.7% |
| Q-9 | 3.3% |
| Q-11 | 0.6% |
| Q-8 | 0.4% |
| Microbial fatty acid analysis: | |
| Component | Area (%) |
| (whole fatty acids) | |
| 3-OH C14:0 | 4.6 |
| C16:1 | 5.9 |
| C16:0 | 14.0 |
| 3-OH C16:0 | 0.1 |
| C18:1 | 70.7 |
| C18:0 | 3.3 |
| unknown | 1.4 |
| (3-OH fatty acids) | |
| 3-OH C14:0 | 88.8 |
| 3-OH C16:0 | 6.6 |
| 3-OH C18:0 | 4.6 |
| (2-OH fatty acid) | |
| not detected | |

Arthrobacter sp. CA 17-2 (FERM BP-4420)

(a) Morphology

Bacillus or coccus, Gram-positive

Spore: −

Mobility: +

Colony: off-white, opaque, round, regular, convex, smooth; diameter ca. 0.5 mm (2 days)

| Growth at: | |
|---|---|
| 30° C. | + |
| 37° C. | (+) |
| 45° C. | − |

(b) Physiological Activities

| | |
|---|---|
| Catalase | + |
| Oxidase | − |
| Glucose fermentation | − |

(c) Chemotaxonomy

Amino acid in peptidoglycan: L-Lysine

Mycolic acid: −

Fatty acid composition:
anteiso $C_{15:0}$ (12-methyltetradecanoic acid) 58%
iso $C_{15:0}$ (13-methyltetradecanoic acid) 5.5%
iso $C_{16:0}$ (14-methylpentadecanoic acid) 8%
anteiso $C_{17:0}$ (14-methylhexadecanoic acid) 25%

The enzyme decarbamylase can be obtained by cultivating the microorganisms usually in a liquid medium in a conventional manner. However, a solid medium may also be used. The medium usually contains assimilable carbon and nitrogen sources as well as inorganic salts essential for the growth of each microorganism. Decarbamylase productivity of the bacteria can be preferably improved by adding to the culture medium a small amount of substance such as an amino acid, for example D-p-hydroxyphenylglycine or D-phenylglycine; an N-carbamyl-α-amino acid, for example N-carbamyl-DL-methionine or N-carbamyl-D-phenylalanine; 5-substituted hydantoin, for example DL-5-p-hydroxyphenylhydantoin or DL-5-phenylhydantoin; a pyrimidine metabolite, for example uracil, dihydrouracil or β-ureidopropionic acid; a metal ion, for example $Fe^{2+}$, $Fe^{3+}$, $Be^{2+}$, $Co^{2+}$, $Al^{3+}$, $Li^+$, $Mn^{2+}$, $Mg^{2+}$ or $Cs^+$; or urea. These additives can be present in the culture medium in a concentration of from 0.1 to 10 mM for the metal ions, and from 0.01 to 1% by weight for the other substrates.

The cultivation can be performed at a temperature in the range of from 20° to 85° C. and at a pH value in the range of from 4 to 11. Aeration and stirring may promote the growth of microorganisms.

After the cultivation, the culture medium or the microorganisms collected therefrom, as such or further processed, may be served as an enzyme source for decarbamylation of the D-N-carbamyl-α-amino acids. Live or dried (for example, lyophilized) bacteria can be used. They may also be served after homogenization, extraction, treatment with a surfactant, or sonication. In addition, pure or crude enzyme recovered from the bacteria homogenate, extract etc. can be used. The pure or crude enzyme can be immobilized according to, for example, the disclosure of the International Application PCT/JP91/01696.

In principle, enzymes produced by gene-manipulated microorganisms are equally useful as those from the original bacteria.

The decarbamylation reaction is performed in an aqueous medium at a pH value in the range of from 6 to 11, preferably from 7 to 9.5. Some enzymes have optimum pH values of from 8 to 9. Decarbamylation takes place usually at a temperature of from 20° to 85° C., the temperature being determined optimally for the particular enzyme.

In the present process, the substrates for decarbamylase are N-carbamyl-D-α-amino acids such as D-N-carbamylalanine, D-N-carbamylmethionine, D-N-carbamylvaline, D-N-carbamylleucine, D-N-carbamylphenylglycine, D-N-carbamyl-(4-hydroxyphenyl)glycine, D-N-carbamyl-(2-thienyl)glycine and D-N-carbamylphenylalanine. The group R in the above mentioned formulae can be, for example, phenyl-, indolyl-, alkylthio-, hydroxyl-, amino- or carboxyl-substituted alkyl.

D-α-Amino acids, the decarbamylation products, can be recovered by conventional procedures such as concentration, neutralization and ion-exchange chromatography. In order to separate a relatively hydrophobic D-α-amino acid such as D-phenylglycine, D-(4-hydroxyphenyl)glycine, D-leucine or D-phenylalanine, the decarbamylation reaction mixture may be acidified or alkalized to precipitate impurities off, and then treated in a conventional manner, for example by concentration and neutralization, to precipitate the amino acids. Separation of a relatively hydrophilic products such as D-thienylglycine, D-serine and D-alanine can be achieved by ion-exchange chromatography. The eluate, for example with an ammonia solution, is then neutralized and concentrated.

The N-carbamyl-D-amino acids as the substrates for decarbamylase can be derived from 5-substituted hydantoin by an enzymatic reaction. As the enzyme source for this reaction, culture media of various microorganisms, the microorganisms collected therefrom (as such or further processed), or enzymes extracted therefrom may be used. These processes are disclosed, for example, in Japanese Patent Kokai Publication Nos. 44690/1978, 69884/1978, 91189/1978, 133688/1978, 84086/1979 and 7001/1980.

The D-carbamyl-α-amino acids are converted to corresponding optically active D-α-amino acids by the present process.

EXAMPLES

The present invention is illustrated by the following Examples.

Example 1

Soli samples (taken from different places in Japan) were placed into 2 ml of a medium A (1 g/l $KH_2PO_4$, 1 g/l $K_2HPO_4$, 0.3 g/l $MgSO_4.7H_2O$, 0.1 g/l yeast extract, 1 g/l $NH_4Cl$, 1.5 g/l a carbon source as listed below; pH 7.0) or a medium B (1 g/l $KH_2PO_4$, 1 g/l $K_2HPO_4$, 0.3 g/l $MgSO_4.7H_2O$, 0.5 g/l glucose, 0.1 g/l yeast extract, 1.5 g/l a nitrogen source as listed below; pH 7.0) and aerobically incubated at 28° C. Microorganisms were multiplicated through subculture in the same medium. Then, the culture medium was spread on an agar plate (containing 2% agar in medium A or B) and incubated at 28° C. for 2 to 6 days to isolate the strains.

Carbon and Nitrogen Sources

N-Carbamyl-D-p-hydroxyphenylglycine (C-D-HPG)

N-Carbamyl-D-phenylglycine (C-D-PG)

N-Carbamyl-D-alanine (C-D-Ala)

DL-5-Methylhydantoin (DL-Ala-hyd)

DL-5-Phenylhydantoin (DL-PG-hyd)

DL-5-p-Hydroxyphenylhydantoin (DL-HPG-hyd)

Citrulline

Phenylurea n-Butyl carbamate

The isolated strain was suspended in 100 μl of a substrate solution (35 mM C-D-HPG, 200 mM potassium phosphate; pH 7.0) and incubated for 1 to 3 days at 28° C. Then, a sample of the suspension was analyzed for the carbamyl-D-HPG and D-HPG contents by TLC on a Merck 60 $F_{254}$ plate. The sample was developed by butanol:acetic acid:water 3:3:1 (v/v/v). The amino acids were detected with a UV lump (254 nm) or by spraying p-(dimethylamino)cinnamaldehyde and ninhydrin. It was found that 1868 strains could assimilate the carbon or nitrogen source as used. Among them, 37 strains produced D-HPG, 16 strains of which brought high D-HPG yields ($\geq 2$ mM).

Example 2

The 16 decarbamylase-producing strains were subjected to a further screening. For this purpose, they were cultured in 1 ml of a medium C (1.5 g/l C-D-HPG, 1 g/l $KH_2PO_4$, 1 g/l $K_2HPO_4$, 0.3 g/l $MgSO_4.7H_2O$, 3 g/l yeast extract, 3 g/l meat extract, 10 g/l glycerol, 2 g/l polypeptone; pH 7.0) for 3 days at 28° C. Then, 1 ml of the culture medium was centrifuged to collect the microorganism, which was suspended in 100 μl of the same substrate solution as used in Example. After 24 hours at 30° C. or 50° C., the suspension was analyzed for the D-HPG content.

A sample of the suspension was subjected to HPLC with a Cosmosil 5 C 18 column (φ 4.6×250 mm, Nacarai Tesque). D-HPG was eluted with water:acetonitrile:phosphoric acid 95:5:0.01 (v/v/v). The D-HPG concentration was determined from absorbance at 254 nm. The results are shown in FIG. 1.

Among the 16 strains, the three strains E 206 a, E 222 C and E 215, which were grown on C-D-Ala as a single carbon source, were very active at 30° C. The D-HPG yield by E 222 C was 30.8 mM at 30° C., while only 3.5 mM at 50° C. Other three strains A 17 p-1, A 17 p-3 and A 17 p-4, which were cultured on C-D-HPG as a single carbon source, were highly active at 50° C. The D-HPG yield by A 17 p-4 amounted to 28.8 mM at 50° C., while only 2.5 mM at 30° C.

Example 3
Substrate Specificity of Decarbamylase

For the determination of substrate specificity of decarbamylase of Comamonas sp. E 222 C and Blastobacter sp. A 17 p-4, these strains were cultured at 28° C. in the medium C (as described in Example 2) for 1 day (E 222 C) and 7 days (A 17 p-4). Three ml of the culture medium was centrifuged to separate the microorganism, which was suspended in 300 µl of a substrate solution (200 mM potassium phosphate, 1% (w/v) a substrate as listed below) and incubated for 24 hours at 30° C. (E 222 C) or 50° C. (A 17 p-4).

As shown in Table 1, both microorganisms had high activity to hydrolyze the N-carbamyl substituted, aliphatic and aromatic D-amino acids. However, N-carbamyl derivatives of the amino acids having polar groups were less hydrolized. Comamonas sp. E 222 C could hydrolize β-ureidopropionic acid. It was also found that Blastobacter sp. A 17 p-4 had a hydantoinase activity.

TABLE 1

Substrate specificity of novel decarbamylase

| | Substrate conversion | |
|---|---|---|
| Substrate | Comamonas sp. E 222 c | Blastobacter sp. A 17 p-4 |
| N-Carbamyl- | | |
| D-alanine | ++++ | +++ |
| D-valine | ++++ | +++ |
| D-leucine | ++++ | +++ |
| D-serine | + | − |
| D-phenylalanine | ++++ | +++ |
| D-phenylglycine | +++ | +++ |
| D-p-hydroxyphenylglycine | +++ | ++ |
| DL-norvaline | ++ | ++ |
| DL-norleucine | ++ | ++ |
| DL-threonine | ++ | ++ |
| DL-threonine | + | − |
| sarcosine | − | − |
| β-Ureidopropionic acid | ++++ | − |
| Ureidosuccinic acid | − | − |
| DL-5-Methylhydantoin | − | ++ |
| DL-5-Phenylhydantoin | − | ++ |
| DL-5-p-Hydroxyphenyl-hydantoin | − | ++ |

Conversion to amino acids:
−: 0%
+: <10%
++: <50%
+++: <80%
++++: 100%

Example 4
Promoters for the Production of Comamonas sp. E 222 C Decarbamylase

A search was made for the substances which could increase the yield of decarbamylase of Comamonas sp. E 222 C.

The strain was cultured in a nutrient medium D (1 g/l $KH_2PO_4$, 1 g/l $K_2HPO_4$, 0.3 g/l $MgSO_4.7H_2O$, 3 g/l yeast extract, 3 g/l meat extract, 10 g/l glycerol, 2 g/l polypeptone; pH 7.0) for 2 days at 28° C. The culture medium additionally contained a substance as listed in FIG. 2 in a concentration of 0.15% (w/v).

Figure 2:
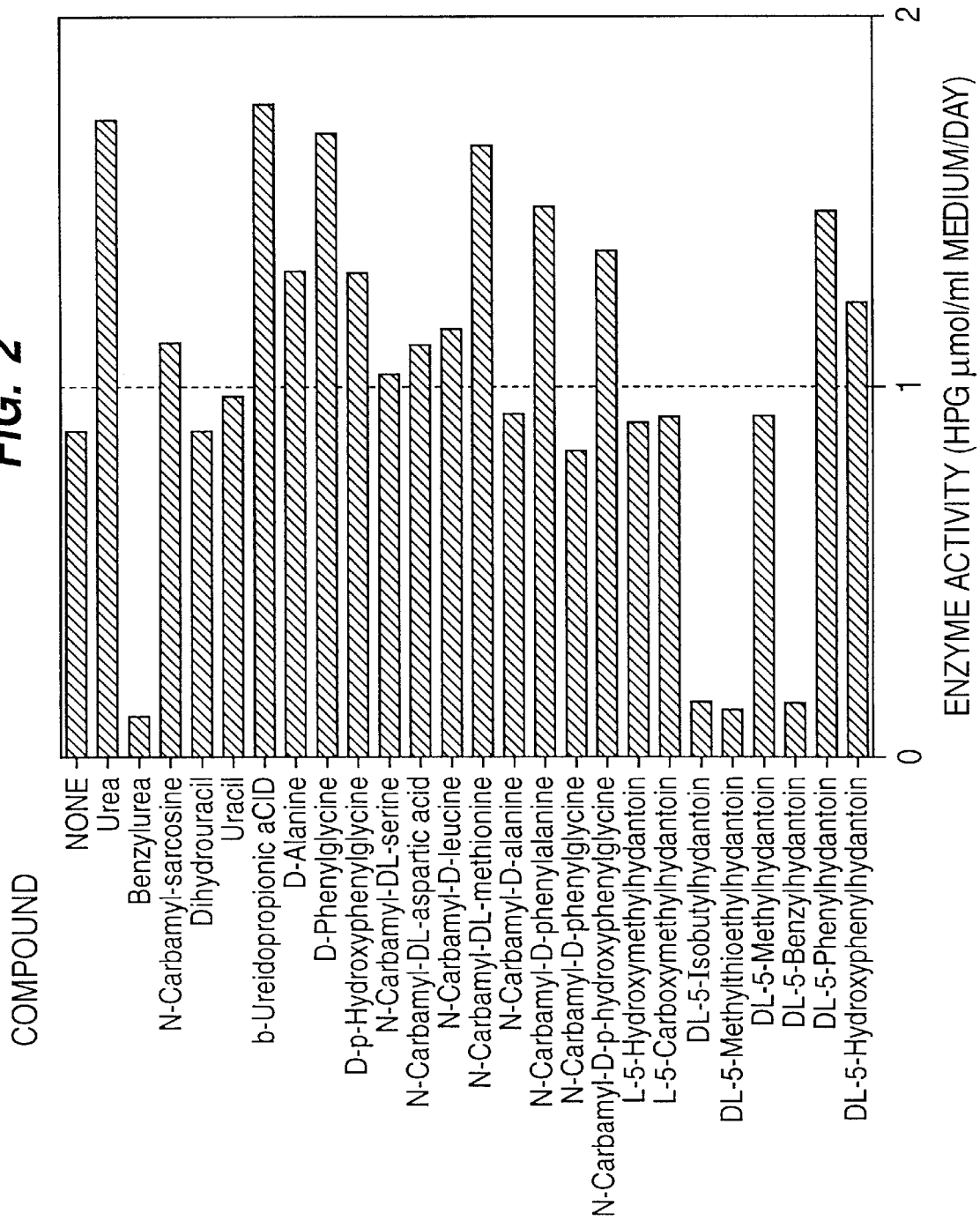
FIG. 2 is a graph showing the effects of various additives to the culture medium of Comamonas sp. E 222 C on its decarbamylase productivity.

One ml of the culture medium was centrifuged to collect the microorganism, which was suspended in 100 µl of a substrate solution (35 mM C-D-HPG, 200 mM potassium phosphate; pH 7.0). After 24 hours at 30° C., D-HPG was quantitated by HPLC according to the procedure described in Example 2. It was found, as shown in FIG. 2, that the decarbamylase productivity could be improved by urea, β-ureidopropionic acid, D-phenylglycine or N-carbamyl-DL-methionine.

Example 5
Purification of Comamonas sp. E 222 C Decarbamylase

Comamonas sp. E 222 C was cultured at 28° C. for 3 days in the medium D (as defined in Example 4) containing 0.15% (w/v) of β-ureidopropionic acid. Total 3.6 l of the culture medium was centrifuged to collect the microorganism, which was suspended in 100 ml of 10 mM potassium phosphate (pH 7.0), homogenized by sonication and then centrifuged to take the supernatant containing the enzyme. Ammonium sulfate was added to the enzyme solution. Precipitation fraction at an ammonium sulfate concentration of 20–40% saturation was centrifuged to separate the enzyme, which was dissolved in the same buffer solution as used above.

Then, 177 ml of the enzyme solution was dialyzed to 10 l of the same buffer for 12 hours, charged into a DEAE-Sephacel column (φ 5×15 cm), and eluted with linear gradient 0 to 1M NaCl. The eluate was adjusted to an NaCl concentration of 4M, charged into a Phenyl-Sepharose CL-4B column (φ 1.5×15 cm), and eluted with linear gradient 4 to 0M NaCl. Thus obtained active fraction was concentrated by ultrafiltration through a YM-10 membrane (Amicon).

The concentrate (5 ml) was gel-filtrated through a Sephacryl S-200 HR column (φ 1.8×80 cm) with the same buffer solution as used above additionally containing 0.2M NaCl. The active fraction was desalted by dialysis, charged into a hydroxyapatite column (φ 1.2×10 cm), eluted with linear gradient 0 to 1M potassium phosphate (pH 7.0). The active eluate (8.5 ml) was dialyzed for 12 hours to 500 ml of 10 mM potassium phosphate (pH 7.0), charged into a Mono Q HR 5/5 column, and eluted with linear gradient 0 to 1.0M NaCl. The thus obtained active fraction (1.2 ml) was analyzed as a purified enzyme solution.

Figure 3:
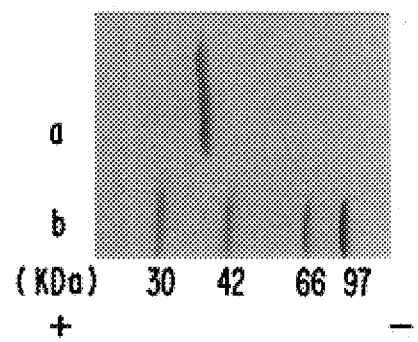
FIG. 3 is a result of SDS-polyacrylamide gel electrophoresis of purified Comamonas sp. E 222 C decarbamylase.

As shown in Table 2, specific activity of the purified enzyme solution was 108 times that of the supernatant of homogenized cell suspension. Enzyme activity recovery was about 2%. Ten mg of the purified enzyme was subjected to SDS-polyacrylamide gel electrophoresis (10% polyacrylamide) according to the King and Laemmli's method [King, J., Laemmli, U. K., Journal of Molecular Biology, Vol. 62, 165–477 (1971)]. A single band was detected at around MW 38,000, as shown in FIG. 3.

TABLE 2

Purification of Comamonas sp. E 222 c decarbamylase

| Purification step | Protein (mg) | Enzyme activity (U) | Specific activity (U/mg) | Recovery (%) |
|---|---|---|---|---|
| 1) Supernatant of cell homogenate | 6316 | 23.5 | 0.0037 | 100 |
| 2) Ammonium sulfate precipitation fraction | 2362 | 21.2 | 0.0090 | 90.2 |
| 3) DEAE-Sephacel fraction | 146 | 21.6 | 0.15 | 91.9 |
| 4) Phenyl-Sepharose fraction | 40.0 | 10.9 | 0.27 | 46.4 |
| 5) Sephacryl S-200 HR fraction | 23.8 | 6.6 | 0.28 | 29.1 |

TABLE 2-continued

Purification of *Comamonas sp.* E 222 c decarbamylase

| Purification step | Protein (mg) | Enzyme activity (U) | Specific activity (U/mg) | Recovery (%) |
|---|---|---|---|---|
| 6) Hydroxyapatite fraction | 2.5 | 0.7 | 0.28 | 3.0 |
| 7) Mono Q HR 5/5 fraction | 1.2 | 0.48 | 0.40 | 2.0 |

Figure 4:
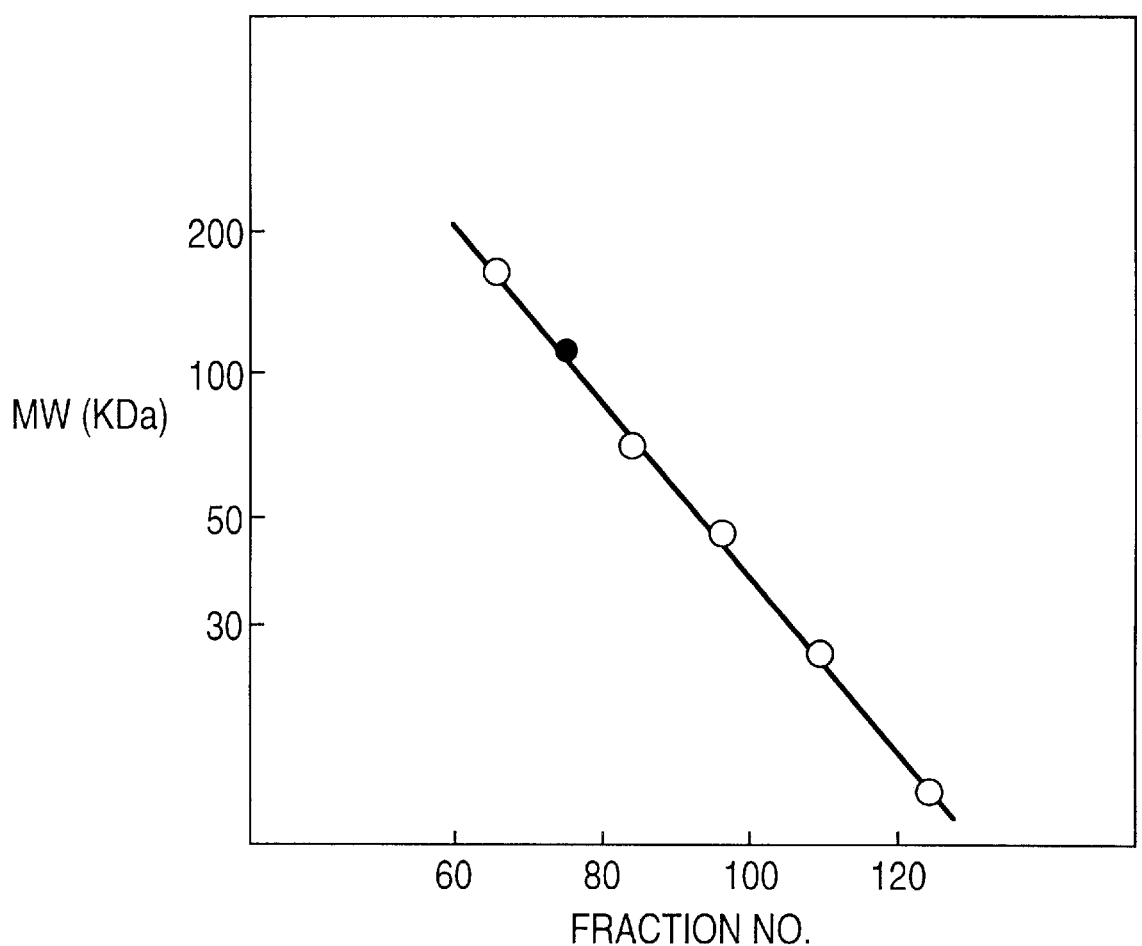
FIG. 4 is a result of gel filtration of the purified Comamonas sp. E 222 C decarbamylase thorough a Sephadex G-150 column.

In addition, the purified enzyme was subjected to gel filtration through a Sephadex G-150 column (φ 1.5×85 cm with 10 mM potassium phosphate (pH 7.0) containing 0.2M NaCl and 0.1 mM dithiothreitol (DTT). The enzyme was eluted at around MW 111,000, as shown in FIG. 4.

Example 6
Characteristics of Comamonas sp. E 222 C Decarbamylase

Optimum pH and temperature of Comamonas sp. E 222 C decarbamylase were determined by using the enzyme solution obtained in Example 5.

Optimum pH was determined as follows: The enzyme solution was contacted with 10 mM N-carbamyl-D-phenylalanine which was buffered with 200 mM acetate-hydrochloride (pH 4.2–5.9), potassium phosphate (pH 5.0–8.8), Tris-hydrochloride (pH 7.6–9.9) or glycine-NaOH (pH 8.9–11.1). (The volume of the mixture was 500 μl.) After the reaction time of 20 minutes at 30° C., the reaction was terminated by the addition of 500 μl of ethanol.

To quantitate D-phenylalanine formed, a sample of the reaction mixture was added to a solution containing 200 mM potassium phosphate (pH 7.0), 1.5 mM 4-aminoantipyrine, 2.1 mM phenol, 2.25 u of peroxidase (obtained from horseradish, CALZYME Lab.) and 0.375 units of D-amino acid oxidase (Sigma) to make the total volume 500 μl. After the mixture was incubated at 37° C. for 60 minutes, increase of absorbance at 500 nm was measured.

Optimum temperature was determined as follows: The enzyme solution was contacted with the same substrate solution as used above (buffered with potassium phosphate pH 7.0) for 20 minutes at 10°–80° C. Then, ammonia formed was quantitated by the indophenol method [Bollter, W. T. et al., Analytical Chemistry, Vol. 33, 592–594 (1961)].

Figure 5:
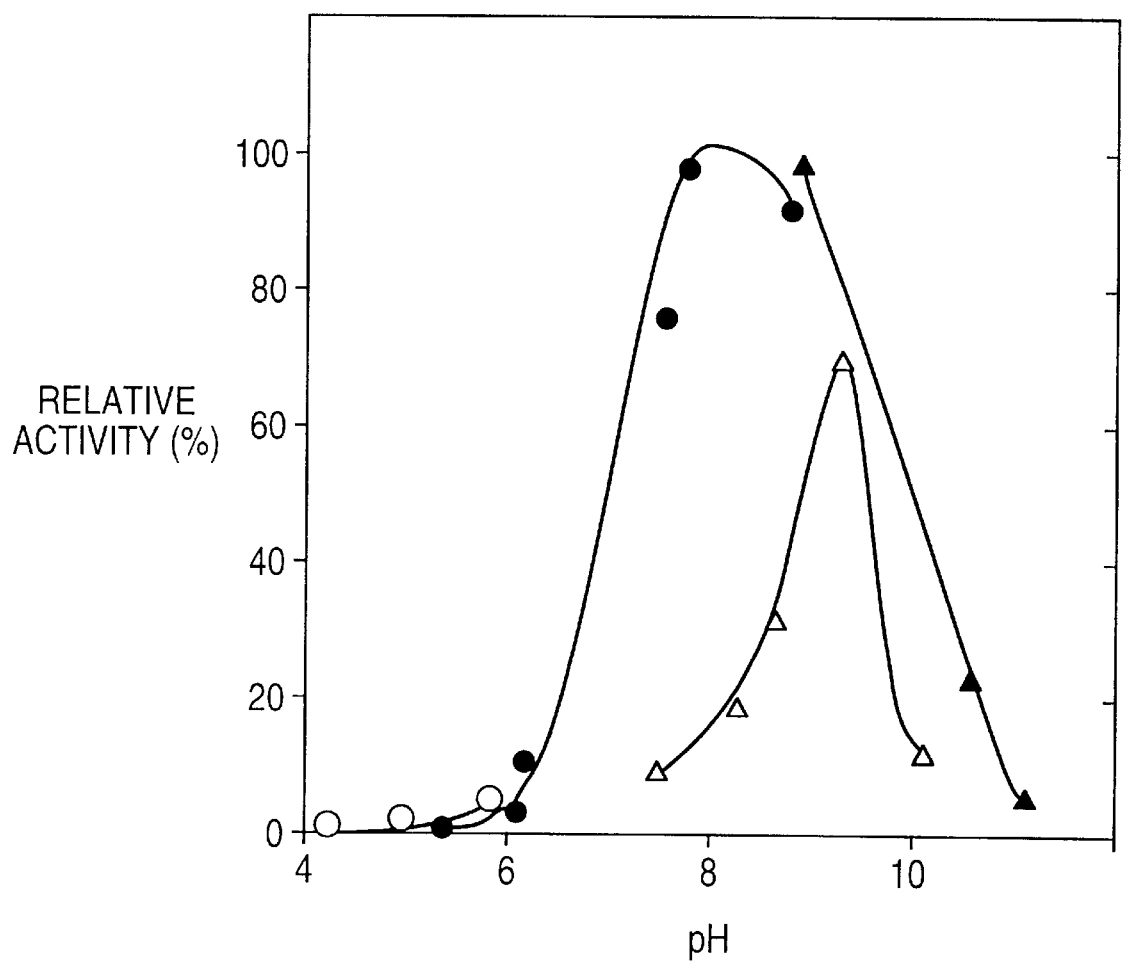
FIG. 5 is a graph showing the effect of pH on the activity of the purified Comamonas sp. E 222 C decarbamylase.
Figure 6:
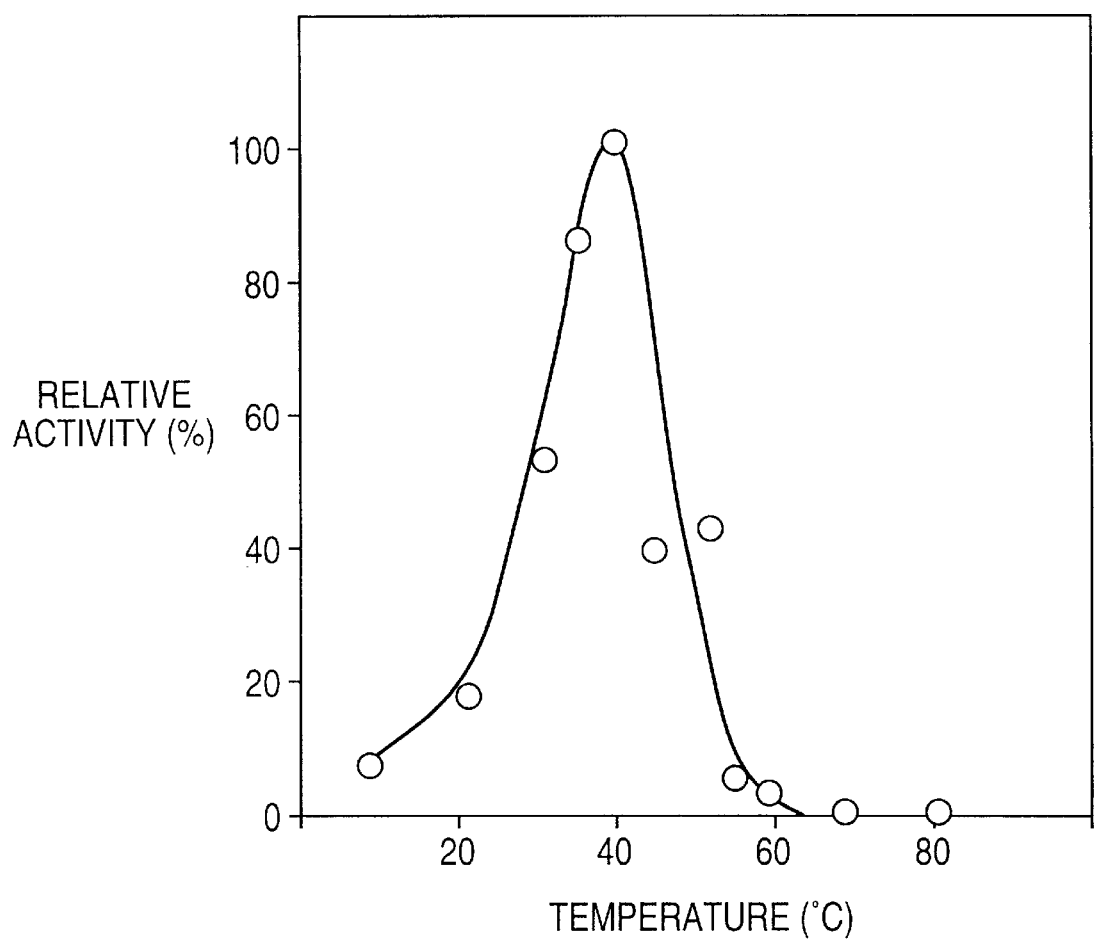
FIG. 6 is a graph showing the effect of temperature on the activity of the purified Comamonas sp. E 222 C decarbamylase.

The results are shown in FIG. 5 and FIG. 6. It was found that the optimum pH and temperature of Comamonas sp. E 222 C decarbamylase were 8–9 and 40° C.

Example 7
Amino Acid Sequence of Comamonas sp. E 222 C Decarbamylase

Amino acid sequence of the protein decarbamylase was determined by using the enzyme solution obtained in Example 5. The enzyme solution was desalted with Centricon-10 Microcentrater (Amicon) and charged into a pulse-liquid protein sequencer. The enzyme had the following amino acid sequence at amino terminal (Arg at 20 and 26 were not confirmed due to unclear peaks): (SEQ ID NO:1)

```
1               5                   10
Ser—Arg—Ile—Val—Asn—Tyr—Ala—Ala—Ala—Gln—Leu—
         15                      20
Gly—Pro—Ile—Gln—Arg—Ala—Asp—Ser—(Arg)—Ala—
              25                      30
Asp—Val—Met—Glu—(Arg)—Leu—Leu—Ala—His
```

Example 8
Promoters for the Production of Blastobacter sp. A 17 p-4 Decarbamylase A search was made for the substances which could increase the yield of decarbamylase of Blastobacter sp. A 17 p-4.

Figure 7:
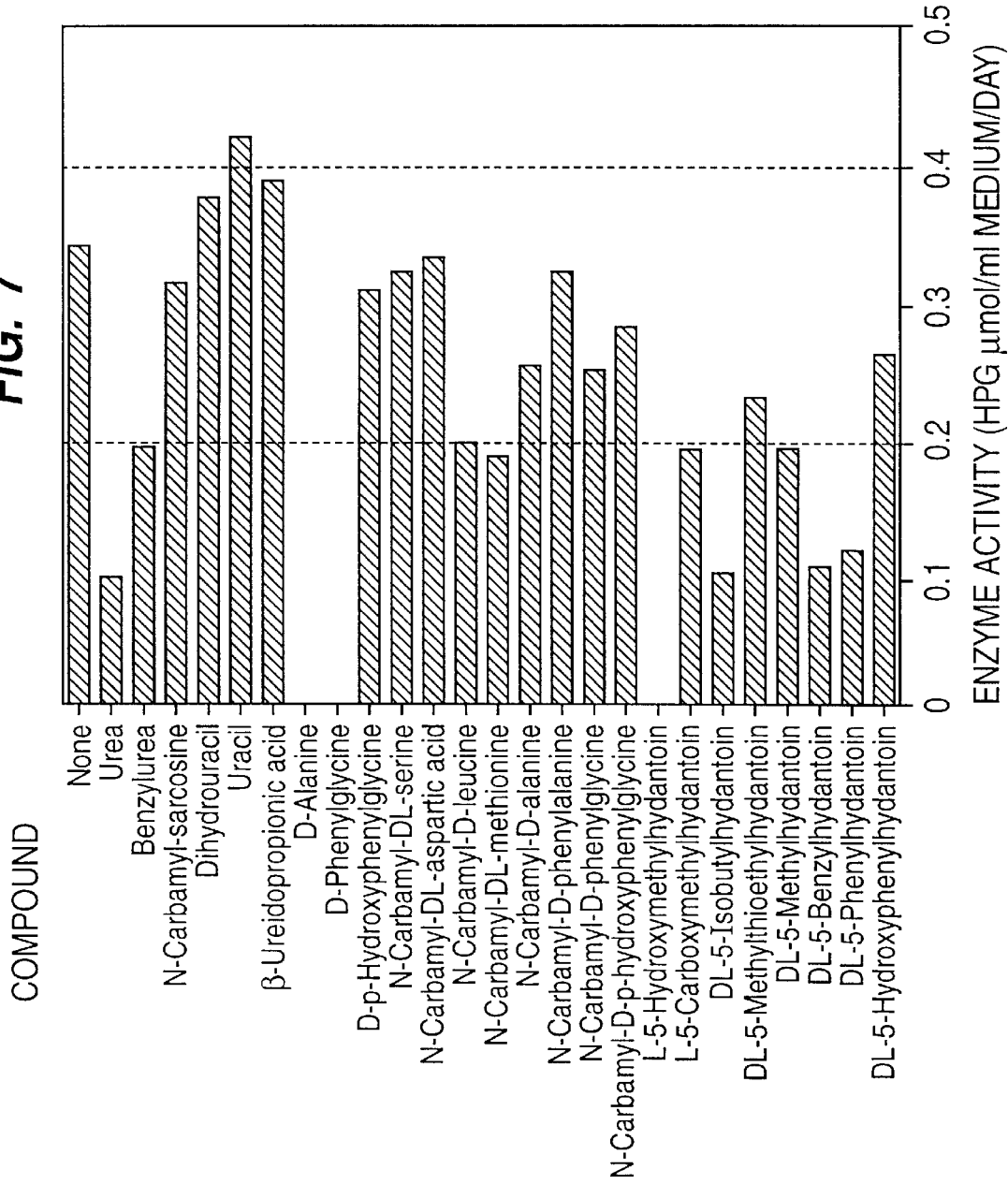
FIG. 7 is a graph showing the effects of various additives to the culture medium of Blastobacter sp. A 17 p-4 on its decarbamylase productivity.

The strain was cultured at 28° C. for 3 days in the medium D (as defined in Example 4) additionally containing 0.15% (w/v) of a substance as listed in FIG. 7. Then, D-HPG was formed in the same way as in Example 4 but that the reaction temperature was 40° C., and quantitated by HPLC. As shown in FIG. 7, the decarbamylase yield was increased in the presence of uracil, dihydrouracil or β-ureidopropionic acid.

Figure 8:
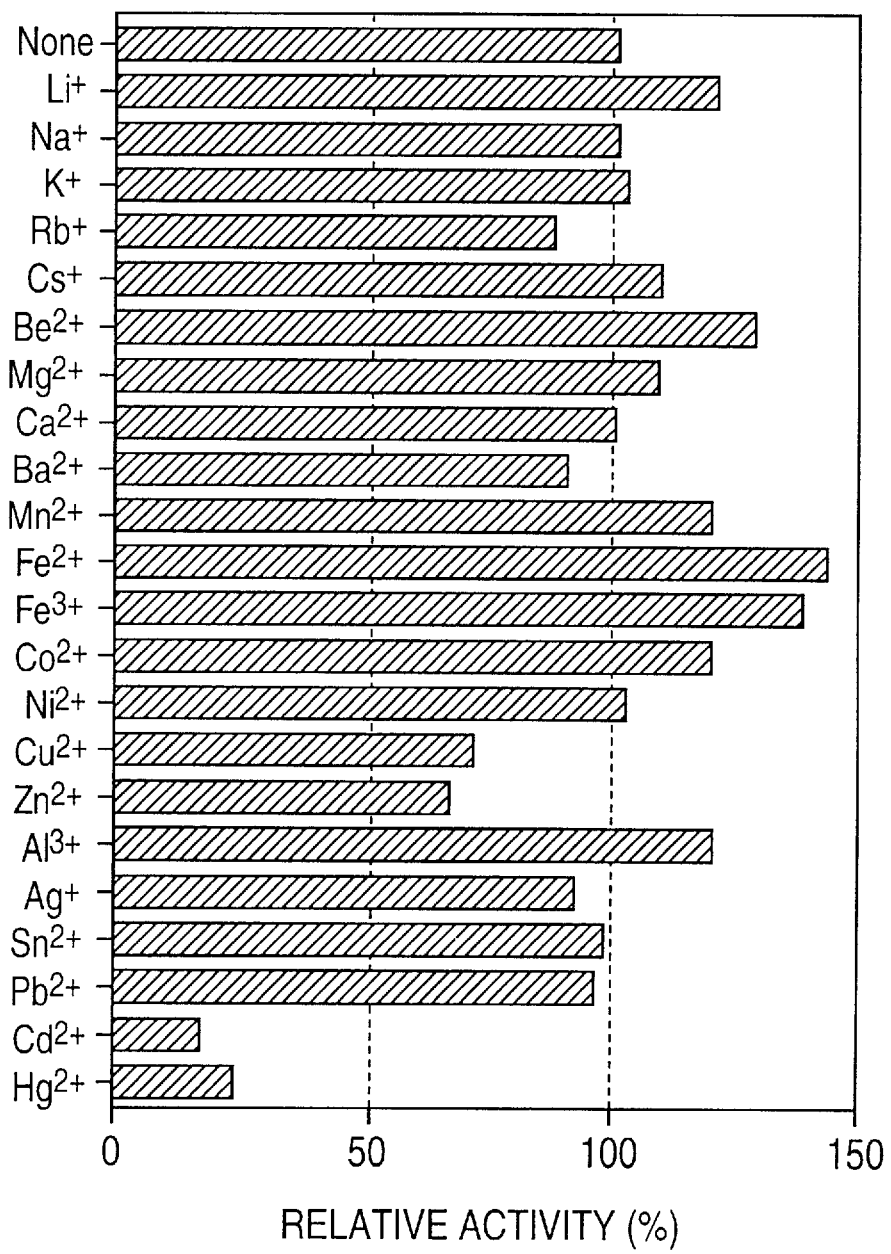
FIG. 8 is a graph showing the effects of various metal ions added to the culture medium of Blastobacter sp. A 17 p-4 on its decarbamylase productivity.

In order to examine the effects of metal ions on the enzyme productivity, the strain was cultured at 28° C. for 4 days in the medium D additionally containing 0.15% (w/v) of uracil and 2 mM a metal ion as listed in FIG. 8. It was found by quantitating D-HPG that ions such as $Fe^{2+}$, $Fe^{3+}$, $Li^+$, $Cs^+$, $Be^{2+}$, $Mg^{2+}$, $Mn^{2+}$, $Co^{2+}$ and $Al^{3+}$ increased the decarbamylase yield.

Example 9
Purification of Blastobacter sp. A 17 p-4 Decarbamylase

Blastobacter sp. A 17 p-4 was cultured at 28° C. for 7 days in the medium D (as defined in Example 4) which additionally containing 0.15% (w/v) of uracil and 2 mM $FeSO_4 \cdot 7H_2O$. Total 4.8 l of the culture medium was centrifuged to separate the microorganism, which was suspended in 120 ml of 10 mM potassium phosphate, homogenized at 5° C. for 20 minutes with glass beads [diameter: 0.25 mm; Dyno-Mill KDL, Switzerland] and centrifuged to obtain a crude enzyme solution as a supernatant. Ammonium sulfate was added to the enzyme solution to take a precipitation fraction at an ammonium sulfate concentration of 20–40% saturation. The precipitate was separated by centrifugation and dissolved in the same buffer solution as used above.

Then, 41 ml of the enzyme solution was dialyzed for 12 hours to 5 l of the same buffer solution as used above, purified with a DEAE-Sephacel column and a Phenyl-Sepharose CL-6B column, and concentrated by ultrafiltration in the same way as in Example 5. The concentrate (3 ml) was gel-filtrated through a Sephadex G-150 column (φ 1.5×80 cm) with the same buffer solution as used above (additionally containing 0.2M NaCl), desalted by dialysis, and purified by the same procedure as in Example 5 with a Mono Q HR 5/5 column. The thus obtained active fraction (2 ml) was analyzed as a purified enzyme solution. As shown in Table 3, specific activity of the purified enzyme solution was 37 times that of the supernatant of homogenized cell suspension. Enzyme activity recovery was 2.3%.

TABLE 3

Purification of *Biastobacter sp.* A 17 p-4 decarbamylase

| Purification step | Protein (mg) | Enzyme activity (U) | Specific activity (U/mg) | Recovery (%) |
|---|---|---|---|---|
| 1) Supernatant of cell homogenate | 4657 | 52.0 | 0.011 | 100 |
| 2) Ammonium sulfate precipitation fraction | 797 | 30.2 | 0.038 | 58.1 |
| 3) DEAE-Sephacel fraction | 284 | 18.3 | 0.064 | 35.2 |
| 4) Phenyl-Cellulose fraction | 89.6 | 7.6 | 0.085 | 14.6 |
| 5) Sephadex G-150 fraction | 15.4 | 4.1 | 0.27 | 7.9 |
| 6) Mono Q HR 5/5 fraction | 2.9 | 1.2 | 0.41 | 2.3 |

Figure 9:
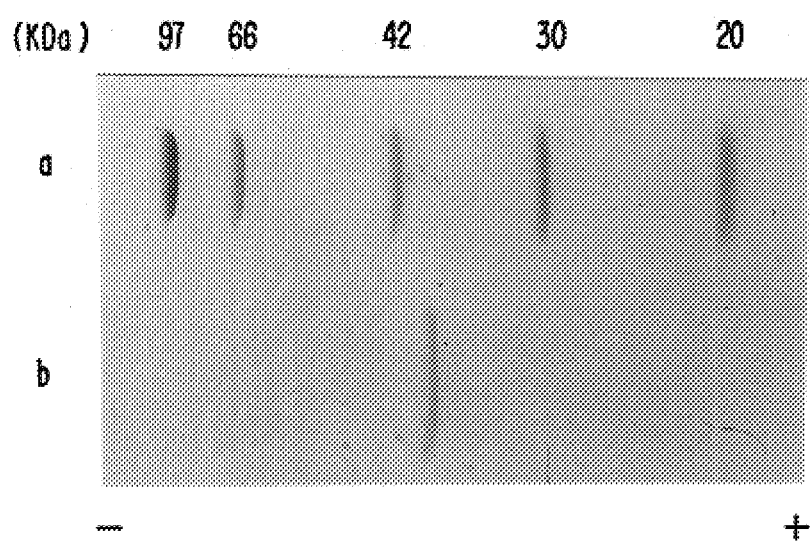
FIG. 9 is a result of SDS-polyacrylamide gel electrophoresis of purified Blastobacter sp. A 17 p-4 decarbamylase.
Figure 10:
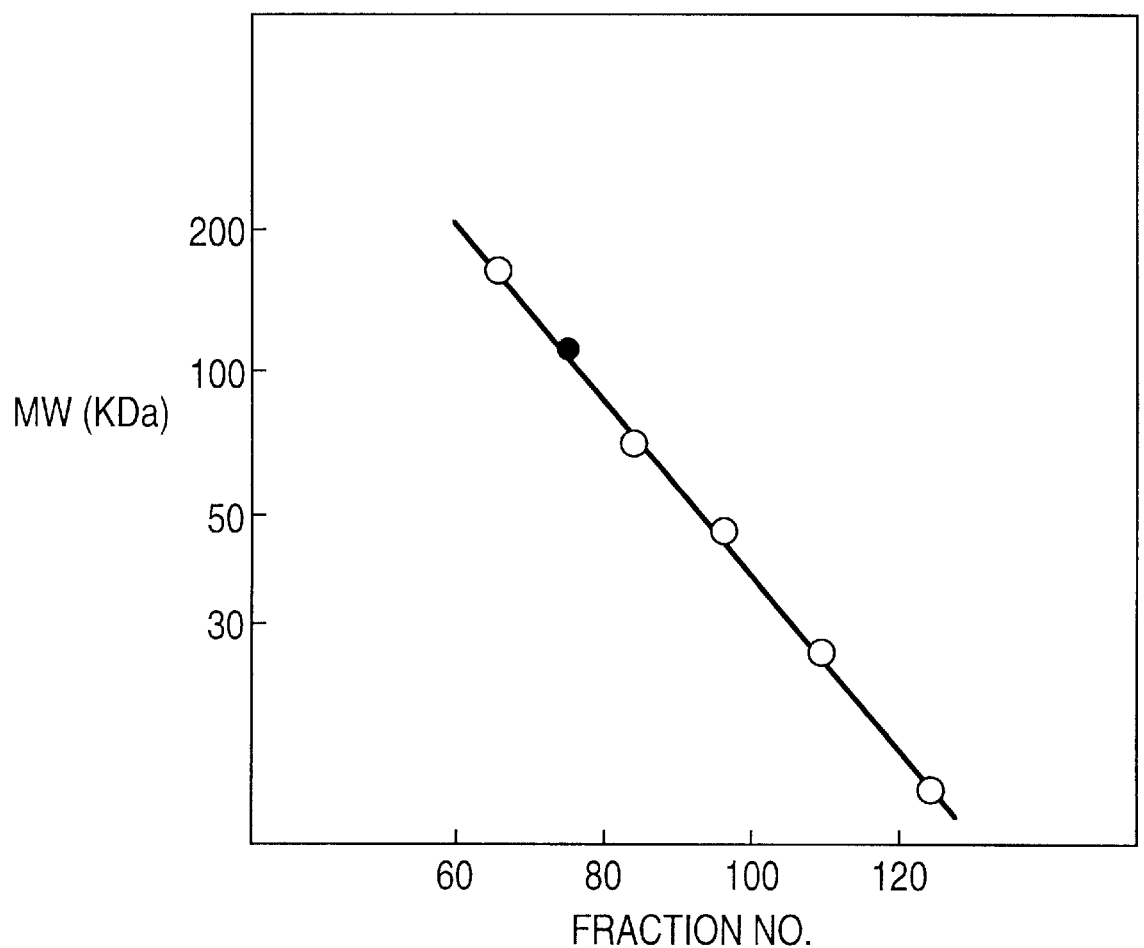
FIG. 10 is a result of gel filtration of the purified Blastobacter sp. A 17 p-4 decarbamylase thorough a Sephadex G-150 column.

The purified enzyme was subjected to SDS-polyacrylamide gel electrophoresis. A single band was detected at around MW 39,000; see FIG. 9. In addition, the purified enzyme was gel-filtrated through a Sephadex G-150 column in the same way as in Example 5. The enzyme was eluted at around MW 120,000; see FIG. 10.

Example 10

Characteristics of Blastobacter sp. A 17 p-4 Decarbamylase

Figure 11:
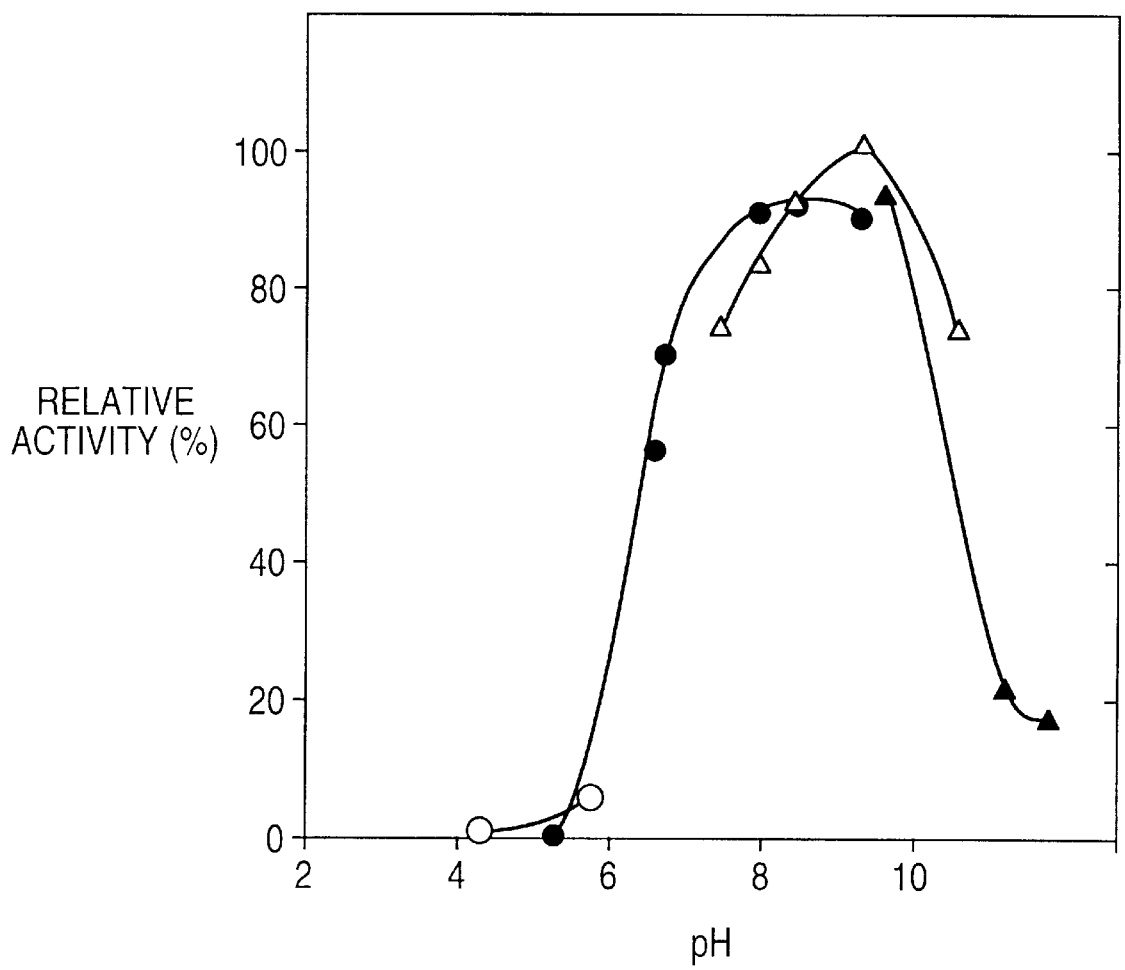
FIG. 11 is a graph showing the effect of pH on the activity of the purified Blastobacter sp. A 17 p-4 decarbamylase.
Figure 12:
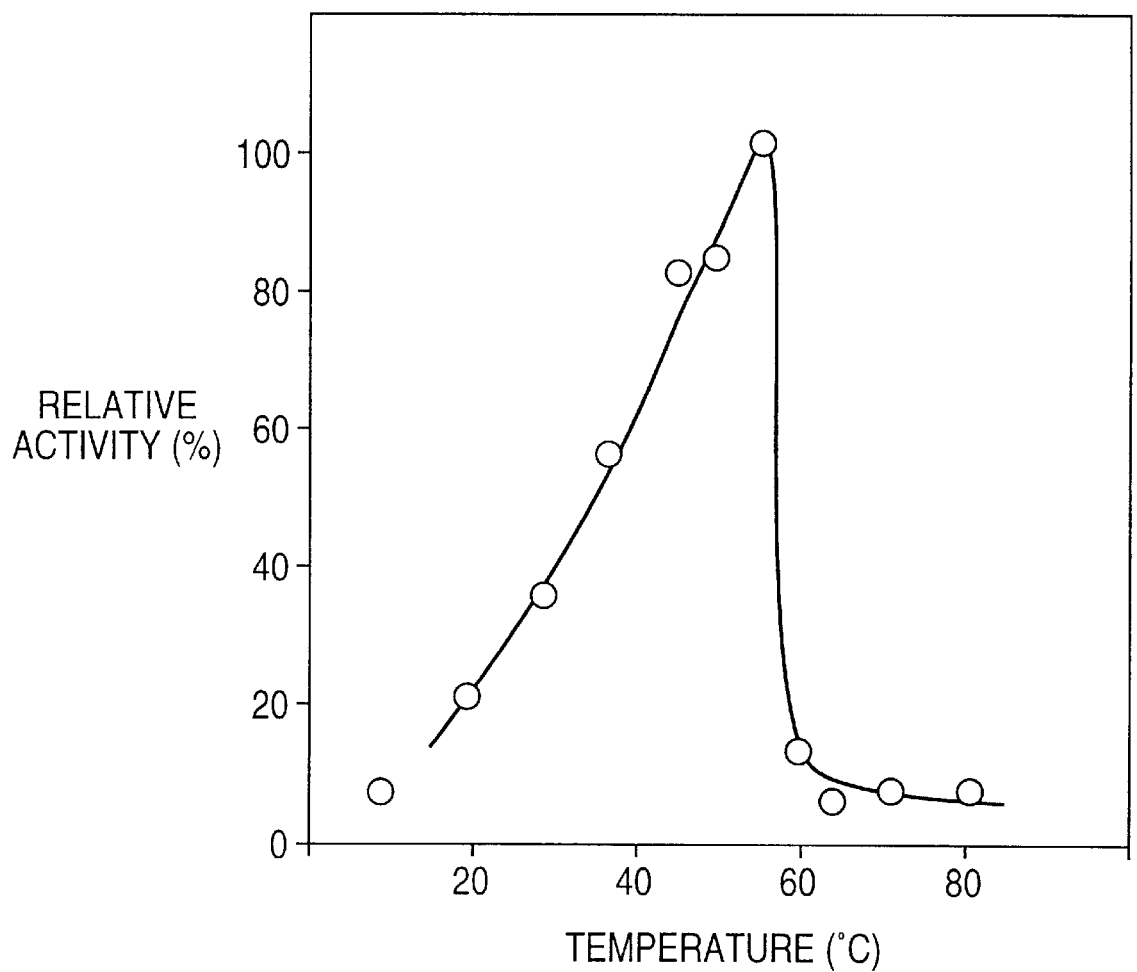
FIG. 12 is a graph showing the effect of temperature on the activity of the purified Blastobacter sp. A 17 p-4 decarbamylase.

Optimum pH and temperature of Blastobacter sp. A 17 p-4 decarbamylase were determined by using the enzyme solution obtained in Example 9 according to the same procedure as in Example 6. The results are shown in FIGS. 11 and 12. It was found that the optimum pH and temperature of Blastobacter sp. A 17 p-4 decarbamylase were 9 and 50° C.

Example 11

Amino Acid Sequence of Blastobacter sp. A 17 p-4 Decarbamylase

Amino acid sequence of the protein decarbamylase was determined by using the enzyme solution obtained in Example 9 according to the same procedure as in Example 7. The enzyme had the following amino acid sequence at amino terminal (Arg at 38 was not confirmed due to unclear peak) (SEQ ID NO:2):

```
 1              5                      10
Ala—Arg—Lys—Leu—Asn—Leu—Ala—Val—Ala—Gln—Leu—
               15                     20
Gly—Pro—Ile—Ala—Arg—Ala—Glu—Thr—Arg—Asp—Gln—
              25                    30
Val—Val—Ala—Arg—Leu—Met—Glu—Met—Met—Lys—Glu—
     35                        40
Ala—Lys—Ser—Ser—(Arg)—Gly—Thr
```

Example 12

The seven strains of the genera Rhizobium and Bradyrhizobium listed in Table 4 were cultured at 30° C. for 24 hours in 1 ml of the 805 liquid medium (yeast extract 1 g/l, mannitol 5 g/l, $K_2HPO_4$ 0.7 g/l, $KH_2PO_4$ 0.1 g/l, $MgSO_4.7H_2O$ 1 g/l, C-D-HPG 1 g/l; pH 7.0) containing C-D-HPG or C-D-Ala in a final concentration of 1 g/l. The culture medium was centrifugated to separate the microorganism, which was suspended in 0.5 ml of a substrate solution (1% C-D-HPG or C-D-Ala, 0.1M potassium phosphate (pH 7.0), 0.1% Triton X-100). The suspension was incubated at 37° C. for 24 hours and analyzed by TLC in the same way as in Example 1. Decarbamylation activity was found in the strains of genus Bradyrhizobium, as shown in Table 4.

TABLE 4

| Strain | Decarbamylase activity |
| --- | --- |
| Rhizobium loti IFO 14779 | ++ |
| Rhizobium meliloti IFO 14782 | ++ |
| Rhizobium Fredii IFO 14780 | ++ |
| Rhizobium galegae IFO 14965 | ++ |
| Rhizobium huakuii IFO 15243 | + |
| Bradyrhyzobium japonicum IFO 14783 | + |
| Bradyrhyzobium sp. IFO 15003 | + |

Example 13

Soil samples were subjected to another screening in the same way as in Example 1. N-Carbamyl-D-leucine (C-D-Leu), N-carbamyl-D-alanine (C-D-Ala), N-carbamyl-D-phenyl-glycine (C-D-PG) or DL-5-methylhydantoin (DL-Ala-hyd) was used as a carbon or nitrogen source. Among the strains which were grown, 9 strains were tested for decarbamylase activity on C-D-Ala or C-D-HPG according to the procedure of Example 12. The results are shown in Table 5. Some strains were more specific to C-D-HPG than to C-D-Ala, and the others more specific to C-D-Ala than to C-D HPG.

TABLE 5

| Strain | Substrate | Activity |
| --- | --- | --- |
| Rhizobium sp. KNK 1415 Alcaligenes xylosoxidans subsp. denitrificans | C-D-PG | +++ (C-D-HPG) |
| CL 66-2a | C-D-Leu | ++ (C-D-HPG) |
| CL 67-1 | C-D-Leu | ++ (C-D-HPG) |
| CL 85-1 | C-D-Leu | + (C-D-HPG) |
| CA 17-1 Arthrobacter sp. | C-D-Ala | + (C-D-Ala) |
| CA 17-2 | C-D-Ala | ++ (C-D-Ala) |
| CA 77-2 | C-D-Ala | ++ (C-D-Ala) |
| AH 71-1 | DL-Ala-hyd | + (C-D-Ala) |
| AH 57-1 | DL-Ala-hyd | ++ (C-D-Ala) |

Example 14

The strain of Rhyzobium sp. KNK 1415 which was obtained in Example 13 was cultured at 30° C. for 40 hours in 10.1 of the SE medium (sucrose 23 g/l, yeast extract 4 g/l, urea 2 g/l, $KH_2PO_4$ 2 g/l, $Na_2HPO_4$ 2 g/l, $MgSO_4.7H_2O$ 1 g/l, $MnCl_2.4H_2O$ 0.01 g/l; pH 6.5). The culture medium was centrifugated to separate the microorganism, which was washed with 0.9% saline, homogenized by sonication, and centrifugated. The supernatant was treated with protamine sulfate (0.1 mg/mg protein) for enucleation and then centrifugated. The supernatant was heated to 50° C. for 30 minutes and centrifugated to remove denatured proteins. To the solution, ammonium sulfate was added in a concentration of 30% saturation. The ammonium sulfate precipitate was collected by centrifugation, dissolved in 500 ml of a buffer solution (20 mM Tris.HCl (pH 7.5), 2 mM DTT), dialyzed to the same buffer solution, charged into a DEAE-cellulose column and eluted with a solution (10 mM sodium phosphate (pH 7.2), 0.15M NaCl, 1 mM DTT). The eluate was concentrated by ultrafiltration with a YM-10 membrane (Amicon) and analyzed by SDS-polyacrylamide gel electrophoresis. The enzyme decarbamylase was detected at around 35,000.

Example 15

The part of decarbamylase band of the SDS-polyacrylamide gel from Example 14 was cut out, homogenized in a buffer solution (50 mM Tris.HCl (pH 7.5), 0.1% SDS, 0.1 mM EDTA, 150 mM NaCl, 5 mM DTT) and eluted at room temperature. The extract was concentrated by ultrafiltration, charged into a reverse phase HPLC column (AP-303; YMC) and eluted with gradient acetonitril. Thus obtained decarbamylase-containing fraction was charged into a gas phase protein sequencer (Applied Biosystems). The enzyme had the following amino acid sequence at amino terminal (SEQ ID NO:3):

```
 1            5                  10
Thr—Arg—Gln—Met—Ile—Leu—Ala—Val—Gly—Gln—
```

Effects of the Invention

By using novel decarbamylase according to the invention, D-α-amino acids, which are important intermediates for the production of pharmaceuticals such as antibiotics, can be prepared more efficiently under convenient conditions such as pH 8–9 and 50° C.

What is claimed is:

1. An isolated decarbamylase produced by a microorganism belonging to the genus Comamonas, having an optimum pH value of from 8 to 9, an optimum temperature of from 40° C. to 50° C., and the amino-terminal sequence of SEQ ID NO:1.

2. The isolated decarbamylase according to claim 1, wherein said microorganism is Comamonas sp. E 222 C.

3. An isolated decarbamylase produced by a microorganism belonging to the genus Blastobacter, having an optimum pH value of from 8 to 9, an optimum temperature of from 40° C. to 50° C., and the amino-terminal sequence of SEQ ID NO:2.

4. The isolated decarbamylase according to claim 3, wherein said microorganism is Blastobacter sp. A 17 p-4.

* * * * *

UNITED STATES PATENT AND TRADEMARK OFFICE
CERTIFICATE OF CORRECTION

PATENT NO. : 5,863,785
DATED : January 26, 1999
INVENTOR(S) : Hideaki YAMADA, et al.

It is certified that error appears in the above-identified patent and that said Letters Patent is hereby corrected as shown below:

On the title page, insert the following:
--[30]   Oct. 1, 1993 [WO] WIPO........PCT/JP93/01408--.

Signed and Sealed this

Thirty-first Day of August, 1999

Attest:

Q. TODD DICKINSON

*Attesting Officer*          *Acting Commissioner of Patents and Trademarks*